(12) United States Patent
Han et al.

(10) Patent No.: US 8,741,603 B2
(45) Date of Patent: Jun. 3, 2014

(54) ENHANCING SPINOSYN PRODUCTION WITH OXYGEN BINDING PROTEINS

(75) Inventors: Lei Han, Carmel, IN (US); Nigel Mouncey, Indianapolis, IN (US)

(73) Assignee: Agrigenetics Inc., Indianapolis, IN (US)

( * ) Notice: Subject to any disclaimer, the term of this patent is extended or adjusted under 35 U.S.C. 154(b) by 134 days.

(21) Appl. No.: 13/100,202

(22) Filed: May 3, 2011

(65) Prior Publication Data

US 2012/0282657 A1 Nov. 8, 2012

(51) Int. Cl.
  *C07K 14/195* (2006.01)
  *C07K 14/805* (2006.01)
  *C12P 19/62* (2006.01)
  *C40B 30/00* (2006.01)

(52) U.S. Cl.
  USPC ............... 435/76; 435/252.3; 435/471; 506/7

(58) Field of Classification Search
  None
  See application file for complete search history.

(56) References Cited

U.S. PATENT DOCUMENTS 5,362,634 A 11/1994 Boeck et al.
5,670,486 A 9/1997 Mynderse et al.

FOREIGN PATENT DOCUMENTS

WO WO93/09126 5/1993
WO 99/46387 9/1999
WO WO 2010-149956 12/2010

OTHER PUBLICATIONS

Brukner et al Genetic engineering of an industrial strain of *Saccharopolyspora erythraea* for stable expression of the *Vitreoscilla* haemoglobin gene (vhb) Microbiology (1998), 144, 2441-2448.*
Rokem et al (Systems biology of antibiotic production by microorganisms Nat. Prod. Rep., 2007, 24, 1262-1287.*
Jin Zhi-hua et al (Improvement of spinosad producing *Saccharopolyspora spinosa* by rational screening Journal of Zhejiang University Science A Jin et 366 al. / J Zhejiang Univ Science A 2006 7(Suppl. II):366-370.*

Minas et al (Improved erythromycin production in a genetically engineered industrial strain of *Saccharopolyspora erythraea* Biotechnol. Prog.,1998, 14, 561.*
DeModena et al. The Production of Cephalosporin C by *Acremonium chrysogenum* is Improved by the Intracellular Expression of a Bacterial Hemoglobin Biotechnology 1993, 11, 926-929.*
Chen W-Q, Yu ZN, Zheng Y-H (2004) Expression of *Vitreoscilla* hemoglobin gene in *Streptomyces fradiae* and its effect on cell growth and synthesis of tylosin. Chin J Antibiot 29: 516-520 Abstract.*
Madduri et al 2001. Genes for the biosynthesis of spinosyns: applications for yield improvement in *Saccharopolyspora spinosa* Journal of Industrial Microbiology & Biotechnology (2001) 27, 399-402.*
Matsushima et al., "Conjugal transfer of cosmid DNA form *Escherichia coli* to *Saccharopolyspora spinosa*: effects of chromosomal insertions on macrolide A83543 production," Gene, 1994, pp. 39-45, vol. 146.
Pulido et al., "Optimization of gene expression in *Streptomyces lividans* by a transcription terminator," Nucleic Acids Research, 1987, pp. 4227-4240, vol. 15, No. 10.
Xia et al., "Construction and functional analysis of engineering bacteria for spinosa-producing," Conference abstract 15th International Symposium on the Biology of Actinomycetes, Aug. 20-25, 2009, Shanghai, China.
Gust et al, "PCR-targeted streptomyces gene replacement identifies a protein domain needed for biosynthesis of the sesquiterpene soil odor geosmin," PNAS, Feb. 18, 2003, pp. 154-1546, vol. 100, No. 4.
Liang, Feng, et al., "Expression of *Vitreoscilla* hemoglobin in *Bacillus thuringiensis* improve the cell density and insecticidal crystal proteins yield," Appl. Microbiol Biotechnol, 2007, pp. 390-397, vol. 74.

Yushuang, Luo, et al., "Promotion of spinosad biosynthesis by chromosomal integration of the *Vitreoscilla* hemoglobin gene in *Saccharopolyspora spinosa*," Life Sciences, Feb. 2012, pp. 172-180, vol. 55, No. 2.

Zhi-Hua, Jin, et al., "Improvement of spinosad producing *Saccharopolyspora spinosa* by rational screening," Journal of Zhejiang, University, Science A, 2006, pp. 366-370, Suppl, II.

* cited by examiner

*Primary Examiner* — Kagnew H Gebreyesus

(74) *Attorney, Agent, or Firm* — Eric J. Kraus; TraskBritt, P.C.

(57) ABSTRACT

The invention describes the integration of polynucleotides into chromosomal DNA of *S. spinosa* species, which are useful for the production of insecticides, integrants thereof, and also to the use of the integrants. The invention includes the stable integration and expression of an oxygen-binding protein, VHb, which results in increased spinosyn production.

21 Claims, 2 Drawing Sheets

SEQUENCE LISTING

```
<160> NUMBER OF SEQ ID NOS: 7

<210> SEQ ID NO 1
<211> LENGTH: 977
<212> TYPE: DNA
<213> ORGANISM: Artificial Sequence
<220> FEATURE:
<223> OTHER INFORMATION: Hemoglobin Gene Expression Cassette

<400> SEQUENCE: 1
aagcttgaat tcgatatcag cccggtacct cgccgccaac ccgtaccacg gcctctgacg      60
gctccggcca agccgcggaa agcgggggcc gggcgccggt ctccaggcgg ccgggtacct     120
ccgaccgcac ggccgcttcc ggagtggtcc ggaagcggcc tgcggagcgc cctgcggggc     180
ggctatcgat tcactccacc gcctgcgcgt acaggtccgc ctccacctgg atgaacacgt     240
ccgcgatcac gccgtacgcc ttgccccacg cgtccaggat gtcgtccgtc gccgcgtcgc     300
ccagcacctc cttgatcgcg cccagcagct cctggcccac gatcgggtag tgcgccgccg     360
ccacgcccgc ctggcagtgc ttcaccgcga tcttcttcac cgccggcagg atcgccggca     420
ggttctcgat gttctgcgcc gccgccagca ccgtcatcgc cagcgccttc ggctgctcca     480
gcgactcctg ccggcccatg tcgaacagcg gccgcacctc cgggtgcttc gcgaacaggt     540
tcttgtagaa cgtggtcgtg atcgtcacgc cgtgctcctt cagcaccggc accgtcgcct     600
```

```
tgatgatgtt gatcgtctgc tggtccagca tatgattgca ctccaccgct gatgacatca    660
gtcgatcata gcacgatcaa cggcactgtt gcaaatagtc ggtggtgata aacttatcat    720 cccctttgc tgatggagct gcacatgaac ccattcaaag gccggcattt tcagcgtgac     780
atcattctgt gggccgtacg ctggtactgc aaatacggca tcagttaccg tgagctgcat    840
tttccgctgc ataaccctgc ttcggggtca ttatagcgat ttttttcggta tatccatcct   900 tttttcgcacg atatacagga ttttgccaaa gggttcgtgt agactttcct tggtgtatcc   960
aacggcgtca gaagctt                                                   977
```

```
<210> SEQ ID NO 2
<211> LENGTH: 22
<212> TYPE: DNA
<213> ORGANISM: Artificial Sequence
<220> FEATURE:
<223> OTHER INFORMATION: aac3-vhb Forward Primer

<400> SEQUENCE: 2
cgctgaaaag cttctgacgc cg                                              22

<210> SEQ ID NO 3
<211> LENGTH: 20
<212> TYPE: DNA
<213> ORGANISM: Artificial Sequence
<220> FEATURE:
<223> OTHER INFORMATION: aac3-vhb Reverse Primer

<400> SEQUENCE: 3
caacccgtac cacggcctct                                                 20

<210> SEQ ID NO 4
<211> LENGTH: 59
<212> TYPE: DNA
<213> ORGANISM: Artificial Sequence
<220> FEATURE:
<223> OTHER INFORMATION: obsA Internal Strep Stem Loop Primer

<400> SEQUENCE: 4
gaagaaggcg gcgtcgaact ggtcgacctc ggtgaggaag gtacctccga ccgcacggc     59

<210> SEQ ID NO 5
<211> LENGTH: 58
<212> TYPE: DNA
<213> ORGANISM: Artificial Sequence
<220> FEATURE:
<223> OTHER INFORMATION: obsA 5' FRT aac3 Primer

<400> SEQUENCE: 5
ggcaatgcgc agagttcgta gtgcgggagc catttgatgt gtaggctgga gctgcttc      58

<210> SEQ ID NO 6
<211> LENGTH: 24
<212> TYPE: DNA
<213> ORGANISM: Artificial Sequence
<220> FEATURE:
<223> OTHER INFORMATION: SynHemo Forward Primer

<400> SEQUENCE: 6
cagacgatca acatcatcaa ggcg                                            24

<210> SEQ ID NO 7
```

```
<211> LENGTH: 20
<212> TYPE: DNA
<213> ORGANISM: Artificial Sequence
<220> FEATURE:
<223> OTHER INFORMATION: SynHemo Reverse Primer

<400> SEQUENCE: 7
acctggatga acacgtccgc                                              20
```

ENHANCING SPINOSYN PRODUCTION WITH OXYGEN BINDING PROTEINS

FIELD OF THE INVENTION

The invention applies to the technical field of molecular genetics wherein genes may be integrated into the chromosome of *Saccharopolyspora spinosa*. One metabolic engineering approach includes the integration and expression of an oxygen binding protein such as a hemoglobin gene within a chromosomal DNA region that results in increased spinosyn production, while at the same time not having a negative effect on growth or other desired metabolic characteristics of *Saccharopolyspora spinosa*.

BACKGROUND

As disclosed in U.S. Pat. No. 5,362,634, fermentation product A83543 is a family of related compounds produced by *Saccharopolyspora spinosa*. The known members of this family have been referred to as factors or components, and each has been given an identifying letter designation. These compounds are hereinafter referred to as spinosyn A, B, etc. The spinosyn compounds are useful for the control of arachnids, nematodes and insects, in particular, Lepidoptera and Diptera species. The compounds are considered environmentally friendly with an appealing toxicological profile.

The naturally produced spinosyn compounds are macrolides consisting of a 21-carbon tetracyclic lactone, which includes the attachment of two deoxysugars: a neutral sugar (rhamnose) and an amino sugar (forosamine) (see Kirst et al. (1991). If the amino sugar is not present, the compounds have been referred to as the pseudoaglycone of A, D, etc., and if the neutral sugar is not present then the compounds have been referred to as the reverse pseudoaglycone of A, D, etc. A more preferred nomenclature is to refer to the pseudoaglycones as spinosyn A 17-Psa, spinosyn D 17-Psa, etc., and to the reverse pseudoaglycones as spinosyn A 9-Psa, spinosyn D 9-Psa, etc.

The naturally produced spinosyn compounds may be produced via fermentation from *S. spinosa* strains NRRL 18395, 18537, 18538, 18539, 18719, 18720, 18743 and 18823 and derivatives therefrom. These cultures have been deposited and made part of the stock culture collection of the Midwest Area Northern Regional Research Center, Agricultural Research Service, United States Department of Agriculture, 1815 North University Street, Peoria, Ill., 61604.

U.S. Pat. No. 5,362,634 and corresponding European Patent No. 0375316 B1 relate to spinosyns A, B, C, D, E, F, G, H, and J. These compounds are said to be produced by culturing a strain of the novel microorganism *Saccharopolyspora spinosa* selected from NRRL 18395, NRRL 18537, NRRL 18538, and NRRL 18539.

WO 93/09126 relates to spinosyns L, M, N, Q, R, S, and T. Also discussed therein are two spinosyn J producing strains: NRRL 18719 and NRRL 18720, and a strain that produces spinosyns Q, R, S, and T: NRRL 18823.

WO 94/20518 and U.S. Pat. No. 5,670,486 relates to spinosyns K, O, P, U, V, W, and Y, and derivatives thereof. Also discussed therein is spinosyn K-producing strain NRRL 18743.

A challenge in producing spinosyn compounds arises from the need to identify and validate neutral sites in the *S. spinosa* genome, wherein a polynucleotide containing a gene expression cassette could be integrated and stably expressed. The introduced gene expression cassette can contain biosynthetic genes that provide a method for producing new derivatives of the spinosyns which may have a different spectrum of insecticidal activity or a gene expression cassette which can increase the titer levels of spinosyns, in addition to other gene expression cassettes which would impart new beneficial characteristics to the existing spinosyn production strains.

It would be advantageous to identify and introduce genes, which result in increased production of spinosyn compounds.

SUMMARY OF THE INVENTION

The present invention relates to methods of polynucleotide integration into chromosomal DNA of *S. spinosa* species, which are useful for the production of insecticides, integrants thereof, and also to the use of the integrants.

The invention further provides a genetically modified host cell that harbors a spinosyn enhancing gene integrated into the *S. spinosa* genome, which results in increased spinosyn production. As such, *S. spinosa* titer levels result in improved A/D production or J/L production in the shake flask fermentation.

The invention further provides a process for integrating an oxygen-binding gene within *S. spinosa*. A particular embodiment of the present invention utilizes the spinosyn enhancing properties encoded by the VHb gene, wherein the VHb gene expression cassette is borne on the chromosome of *S. spinosa*. The expression of the VHb gene results in improved and increased spinosyn production. As such, A/D spinosyn production in the shake flask fermentation of *S. spinosa* is increased.

DETAILED DESCRIPTION OF THE INVENTION

There are many uses for integrated genes within the chromosome of *Saccharopolyspora spinosa*. The cloned genes, either native or heterologous, can be used to improve yields of spinosyns and to produce new spinosyns. Improved yields can be obtained by integrating into the genome of a strain a duplicate copy of the gene for whatever enzyme is rate limiting in that strain. In cases wherein the biosynthetic pathway is blocked in a particular mutant strain due to lack of a required enzyme, production of the desired spinosyns can be restored by integrating a copy of the required gene. Wherein a biosynthetic pathway is disrupted, a different precursor strain can be created.

This application illustrates that the over expression of the *Vitreoscilla* hemoglobin gene sequence, hereinafter "VHb", in *S. spinosa* results in increased spinosyn production. For *S. spinosa* strain improvement, the stable transformation of a polynucleotide was made by integrating a gene expression cassette into the genome of *S. spinosa*. Integration of the gene via homologous recombination using a part of chromosomal DNA and an insertion element was accomplished. The chromosomal DNA can be inserted into the *S. spinosa* genome. Based on this recombination and as a result of application thereof, the aac(3) IV and VHb gene expression cassettes were separately integrated into the chromosome of *S. spinosa* at the obscurin polyketide synthase (PKS) locus resulting in the inactivation of a native gene, obsA.

The following definitions are used herein and should be referred to for interpretation of the claims and the specification. Unless otherwise noted, all U.S. Patents and U.S. Patent Applications referenced herein are incorporated by reference in their entirety.

As used herein, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As used herein, the terms "comprising" and "including" mean the presence of the stated features, integers, steps, or components as referred to in the claims, but that it does not preclude the presence or addition of one or more other features, integers, steps, components or groups thereof. This means a composition, a mixture, a process, a method, an article, or an apparatus that "comprises" or "includes" a list of elements is not limited to only those elements but may include others not expressly listed or inherent to it. As used herein, "or" refers to an inclusive and an exclusive "or". For example, a condition A or B is satisfied by any one of the following: A is true (or present) and B is false (or not present), A is false (or not present) and B is true (or present), and both A and B are true (or present).

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "invention" or "present invention" is a non-limiting term and is intended to encompass all possible variations as described in the specification and recited in the claims.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. The peptides may comprise L-amino acids.

As used herein, the terms "peptide of interest", "POI", "gene product", "target gene product", and "target coding region gene product" refer to the desired heterologous peptide/protein product encoded by the recombinantly expressed foreign gene. The peptide of interest may include any peptide/protein product including, but not limited to proteins, fusion proteins, enzymes, peptides, polypeptides, and oligopeptides. The peptide of interest ranges in size from 2 to 398 amino acids in length.

As used herein, the term "genetic construct" refers to a series of contiguous nucleic acids useful for modulating genotype or phenotype of an organism. Non-limiting examples of genetic constructs include but are not limited to a nucleic acid molecule, and open reading frame, a gene, an expression cassette, a vector, a plasmid and the like.

As used herein, the term "endogenous gene" refers to a native gene in its natural location in the genome of an organism.

As used herein, a "foreign gene" refers to a gene not normally found in the host organism, but that is introduced into the host organism by gene transfer. Foreign genes can comprise native genes inserted into a non-native organism, or chimeric genes.

As used herein, the term "heterologous" with respect to sequence within a particular organism/genome indicates that the sequence originates from a foreign species, or, if from the same species, is substantially modified from its native form in composition and/or genomic locus by deliberate human intervention. Thus, for example, heterologous gene expression refers to the process of expressing a gene from one organism/genome by placing it into the genome of a different organism/genome.

As used herein, the term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

As used herein, the term "disrupted" or "disruption" when referring to a gene that has been manipulated or modified through genetic engineering or through natural causes that change the activity of a gene. Such gene activity may be increased or decreased. Additionally, such disruption may abolish protein function. To facilitate such a decrease, the copy number of the genes may be decreased, such as for instance by underexpression or disruption of a gene. A gene is said to be "underexpressed" if the level of transcription of said gene is reduced in comparison to the wild type gene. This may be measured by for instance Northern blot analysis quantifying the amount of mRNA as an indication for gene expression. As used herein, a gene is underexpressed if the amount of generated mRNA is decreased by at least 1%, 2%, 5% 10%, 25%, 50%, 75%, 100%, 200% or even more than 500%, compared to the amount of mRNA generated from a wild-type gene. Alternatively, a weak promoter may be used to direct the expression of the polynucleotide. In another embodiment, the promoter, regulatory region and/or the ribosome binding site upstream of the gene can be altered to achieve the reduced expression. The expression may also be reduced by decreasing the relative half-life of the messenger RNA. In another embodiment, the activity of the polypeptide itself may be decreased by employing one or more mutations in the polypeptide amino acid sequence, which decrease the activity. For example, altering the affinity of the polypeptide for its corresponding substrate may result in reduced activity. Likewise, the relative half-life of the polypeptide may be decreased. In either scenario, that being reduced gene expression or reduced activity, the reduction may be achieved by altering the composition of the cell culture media and/or methods used for culturing. "Reduced expression" or "reduced activity" as used herein means a decrease of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are reduced. The activity of the VHb protein may also be reduced by contacting the protein with a specific or general inhibitor of its activity. The terms "reduced activity", "decreased or abolished activity" are used interchangeably herein.

In another embodiment, the promoter, regulatory region and/or the ribosome binding site upstream of the gene can be altered to achieve increased expression. The overexpression may also be reduced by increasing the relative half-life of the messenger RNA. In another embodiment, the activity of the polypeptide itself may be increased by employing one or more mutations in the polypeptide amino acid sequence, which increased the activity. For example, altering the affinity of the polypeptide for its corresponding substrate may result in increased activity. Likewise, the relative half-life of the polypeptide may be increased. In either scenario, that being gene overexpression or increased activity, the increase may be achieved by altering the composition of the cell culture media and/or methods used for culturing. "Overexpression" or "increased activity" as used herein means an increase of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are reduced. The activity of the VHb protein may also be increased by contacting the protein with a specific or general inhibitor of its activity. The terms "Overexpression" and "increased activity" may be used interchangeably.

Expression "control sequences" refers collectively to promoter sequences, ribosome binding sites, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biolog—Hybridization with Nucleic Acid Probes part I chapter 2 Overview of principles of hybridization and the strategy of nucleic acid probe assays, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids, which have more than 100 complementary residues on a filter in a Southern or Northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) Molecular Cloning—A Laboratory Manual (2nd ed.) Vol. 1-3, Cold Spring Harbor Laboratory, Cold Spring Harbor Press, N.Y., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids, which do not hybridize to each other under stringent conditions are still substantially identical if the polypeptides which they encode are substantially identical. This occurs, e.g., when a copy of a nucleic acid is created using the maximum codon degeneracy permitted by the genetic code.

The invention also relates to an isolated polynucleotide hybridizable under stringent conditions, preferably under highly stringent conditions, to a polynucleotide as of the present invention.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in this application or the complement thereof.

Another non-limiting example of stringent hybridization conditions are hybridization in 6× sodium chloride/sodium citrate (SSC) at about 45° C., followed by one or more washes in 1×SSC, 0.1% SDS at 50° C., preferably at 55° C. more preferably at 60° C. and even more preferably at 65° C.

Highly stringent conditions can include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5× SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

In some embodiments an isolated nucleic acid molecule of the invention that hybridizes under highly stringent conditions to a nucleotide sequence of the invention can correspond to a naturally-occurring nucleic acid molecule. As used herein, a "naturally-occurring" nucleic acid molecule refers to an RNA or DNA molecule having a nucleotide sequence that occurs in nature (e.g., encodes a natural protein).

A skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

A cloned fragment of DNA containing genes for spinosyn biosynthetic enzymes would enable duplication of genes coding for rate limiting enzymes in the production of spinosyns. This could be used to increase yield in any circumstance when one of the encoded activities limited synthesis of the desired spinosyn. A yield increase in spinosyn A/D was observed when genes linked to the spinosyn polyketide synthase were duplicated by integrating a cosmid containing them into *S. spinosa* (Madduri et al., 2001). In another example, a yield increase of this type was achieved in fermentations of *Streptomyces fradiae* by duplicating the gene encoding a rate-limiting methyltransferase that converts macrocin to tylosin (Baltz et al., 1997).

Specific intermediates (or their natural derivatives) could be synthesized by mutant strains of *S. spinosa* in which certain genes encoding enzymes for spinosyn biosynthesis have been disrupted. Such strains can be generated by integrating, via homologous recombination, a mutagenic plasmid containing an internal fragment of the target gene. Upon plasmid integration, two incomplete copies of the biosynthetic gene are formed, thereby eliminating the enzymatic function it encoded. The substrate for this enzyme, or some natural derivative thereof, should accumulate upon fermentation of the mutant strain. Such a strategy was used effectively to generate a strain of *Saccharopolyspora erythraea* producing novel 6-deoxyerythromycin derivatives (Weber & McAlpine, 1992).

Such strains could be generated by swapping the target region, via double crossover homologous recombination, with a mutagenic plasmid containing the new fragment between non-mutated sequences, which flank the target region. The hybrid gene would produce protein with altered functions, either lacking an activity or performing a novel enzymatic transformation. A new derivative would accumulate upon fermentation of the mutant strain. Such a strategy was used to generate a strain of *Saccharopolyspora erythraea* producing a novel anhydroerythromycin derivative (Donadio et al., 1993).

Spinosyn biosynthetic genes and related ORFs were cloned and the DNA sequence of each was determined The cloned genes and ORFs are designated hereinafter as spnA, spnB, spnC, spnD, spnE, spnF, spnG, spnH, spnI, spnJ, spnK, spnL, spnM, spnN, spnO, spnP, spnQ, spnR, spnS, ORFL15, ORFL16, ORFR1, ORFR2, *S. spinosa* gtt, *S. spinosa* gdh, *S. spinosa epi*, and *S. spinosa* kre.

*Saccharapolyspora spinosa* produces a mixture of nine closely related compounds collectively called "spinosyns". Within the mixture, spinosyn A and D, known as spinsoad, are the major components and have the highest activity against key insect targets. Spinosyn J and L, two of the minor components within the spinosyn mixture, are the precursors for spinetoram, the second generation spinosyn insecticide.

Spinosad is an insecticide produced by Dow AgroSciences (Indianapolis, Ind.) that is comprised mainly of approximately 85% spinosyn A and approximately 15% spinosyn D. Spinosyn A and D are natural products produced by fermentation of *Saccharopolyspora spinosa*, as disclosed in U.S. Pat. No. 5,362,634. Spinosad is an active ingredient of several insecticidal formulations available commercially from Dow AgroSciences, including the TRACER™, SUCCESS™, SPINTOR™, and CONSERVE™ insect control products. For example, the TRACER product is comprised of about 44% to about 48% spinosad (w/v), or about 4 pounds of spinosad per gallon. Spinosyn compounds in granular and liquid formulations have established utility for the control of arachnids, nematodes, and insects, in particular Lepidoptera, Thysanoptera, and Diptera species. Spinosyn A and D is also referred to herein as Spinosyn A/D.

Spinetoram is a mixture of 5,6-dihydro-3'-ethoxy spinosyn J (major component) and 3'-ethoxy spinosyn L produced by Dow AgroSciences. The mixture can be prepared by ethoxylating a mixture of spinosyn J and spinosyn L, followed by hydrogenation. The 5,6 double bond of spinosyn J and its 3'-ethoxy is hydrogenated much more readily than that of spinosyn L and its 3'-ethoxy derivative, due to steric hindrance by the methyl group at C-5 in spinosyn L and its 3'-ethoxy derivative. See, U.S. Pat. No. 6,001,981. Spinosyn J and L is also referred to herein as Spinosyn J/L.

It has been demonstrated in this application that the over expression of VHb, in *S. spinosa* results in increased spinosyn production. Expression of the oxygen carrier protein, VHb, produces elevated levels of the homodimeric hemoglobin under hypoxic growth conditions (Zhang et al., 2007). Among hemoglobins VHb has an average oxygen association rate constant and a rather high oxygen dissociation rate constant (hundreds times higher than other hemoglobins). This suggests that VHb is able to release the bound oxygen more readily than all other hemoglobins (Zhang et al., 2007). It has been shown that expression of the *Vitreoscilla* hemoglobin gene in heterologous hosts often enhances cell growth and protein production under oxygen-limited conditions (Khosla & Bailey, 1988; Khosla et al., 1990).

Expression of VHb in several *Actinomyces* strains led to increased antibiotic production including chlortetracycline, monensin, erythromycin and actinorhodin (Zhang et al., 2007; Magnolo et al., 1991). The recombinant *Streptomyces coelicolor* strain expressing VHb produced ten fold more actinorhodin than the wild-type strain under low DO levels (DO below 5% of air saturation) (Magnolo et al., 1991). In addition actinorhodin production by the VHb-expressing recombinant strain was less susceptible to aeration conditions. Although erythromycin production is in general not considered sensitive to DO levels as long as the DO levels are above the minimal levels required for growth, expression of VHb in an industrial erythromycin-producing strain significantly increased erythromycin titers to 7.25 g/L from 4.25 g/L while reduced biomass accumulation under fed-batch bioreactor fermentation conditions at scales between 10-15 liters (Brünker et al., 1997; 1998; Minas et al., 1998).

Embodiments of the present invention provide for a genetically modified host cell that harbors a spinosyn enhancing gene integrated into the S. spinosa genome. The enhancing gene can encode for an oxygen-binding protein. Furthermore, the oxygen-binding protein can be any protein, which binds oxygen, particularly those which bind oxygen reversibly such as the globins. Preferred oxygen-binding proteins are those, which are capable of increasing spinosyn production in S. spinosa.

Oxygen-binding proteins that may be used in the invention include, but are not limited to, Vitreoscilla hemoglobin (VHb), Alcaligenes eutrophus flavohemoprotein, horse heart myoglobin, E. coli hemoprotein, B. subtilis hemoprotein, yeast flavohemoglobin, soybean leghemoglobin, lupin leghemoglobin, and sperm whale myoglobin. As noted above, the oxygen-binding protein may also be one that is endogenous to the spinosyn-producing organism.

Genes encoding a large number of oxygen-binding proteins have been cloned and their sequence determined For example, known polynucleotide sequences of globin proteins useful in the instant invention include but are not limited to those encoding a cyanobacterium myoglobin (Potts et al., 1992, Science 256:1690-1692), *Scapharca inaequivalvis* hemoglobin (Gambacurta et al., 1993, FEBS Lett. 330:90-94), *Aplysia limacina* myoglobin (Cutruzzola et al, 1996, Biochem. J. 314:83-90), Ascaris hemoglobin (Sherman et al, 1992, Proc. Natl. Acad. Sci. USA 89:11696-11700), *Pseudoterranova decipiens* nematode hemoglobin (Dixon et al, 1991, Natl. Acad. Sci. USA 88:5655-5659, and Dixon et al, 1992, J. Mol. Evol. 35:131-136). *Paramecium caudatum* hemoglobin (Yamauchi et al, 1992, Biochem. Biophvs. Res. Commun 182:195-200), *Rhizobium meliloti* hemoprotein (David et al., 1988, Cell 54:671-683), and *Saccharomyces cerevisiae* (Shimada et al., 1989, J. Biochem. 105:417-422). Particularly suitable for use in the present invention are those oxygen-binding proteins which have relatively high $k_{off}$ rates such as VHb ($k_{off}$ 5600 $s^{-1}$; Orii and Webster, 1986, J. Biol. Chem. 261:3544-3547) or relatively low oxygen affinity such as horse heart myoglobin ($K_D$ 0.79 μM; Wittenberg et al., 1985, in nitrogen fixation research progress. H. J. Evand et al. Eds. Martinus Nijhoff Publishers, Dordrecht, p. 354). Therefore, preferred oxygen binding proteins can be those proteins with a $k_{off}$ rate for oxygen of greater than 10 $s^{-1}$, more preferred greater than 100 $s^{-1}$, or a $K_D$ for oxygen of more than 0.5 μM, although it will be understood that oxygen-binding proteins with rate constants outside of these parameters will also be useful. As noted earlier, those preferred oxygen-binding proteins include globins such as hemoglobin, myoglobin, and leghemoglobins. The properties of many oxygen-binding proteins, including globins, are disclosed throughout the literature. Additionally, techniques for determining the oxygen-binding properties of a protein such as a globin are well known to one of skill in the art and can be performed without undue experimentation.

As noted earlier one such oxygen-binding protein for use in the instant invention, as described herein by way of working example, is VHb. The complete sequence of the VHb gene is described in U.S. Pat. No. 5,049,493. Mutants of VHb, which bind oxygen are also within the scope of the present invention.

Mutants include, but are not limited to "functional polymorphism(s)" which as used herein refers to a change in the base pair sequence of a gene that produces a qualitative or quantitative change in the activity of the protein encoded by that gene (e.g., a change in specificity of activity; a change in level of activity). The term "functional polymorphism" includes mutations, deletions and insertions.

In general, the step of detecting the polymorphism of interest may be carried out by collecting a biological sample containing DNA from the source, and then determining the presence or absence of DNA containing the polymorphism of interest in the biological sample.

Determining the presence or absence of DNA encoding a particular mutation may be carried out with an oligonucleotide probe labeled with a suitable detectable group, and/or by means of an amplification reaction such as a polymerase chain reaction or ligase chain reaction (the product of which amplification reaction may then be detected with a labeled oligonucleotide probe or a number of other techniques). Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al.

Amplification of a selected, or target, nucleic acid sequence may be carried out by any suitable means. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "3SR") (see J. Guatelli et al., Proc. Natl. Acad. Sci. USA 87, 1874-1878 (1990)), the Qβ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. Such probes may be from 5 to 500 nucleotides in length, preferably 5 to 250, more preferably 5 to 100 or 5 to 50 nucleic acids. When PCR conditions allow for amplification of all allelic types, the types can be distinguished by hybridization with an allelic specific probe, by restriction endonuclease digestion, by electrophoresis on denaturing gradient gels, or other techniques.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

DNA amplification techniques such as the foregoing can involve the use of a probe, a pair of probes, or two pairs of probes, which specifically bind to DNA containing the functional polymorphism, but do not bind to DNA that does not contain the functional polymorphism. Alternatively, the probe or pair of probes could bind to DNA that both does and does not contain the functional polymorphism, but produce or amplify a product (e.g., an elongation product) in which a detectable difference may be ascertained (e.g., a shorter product, where the functional polymorphism is a deletion mutation). Such probes can be generated in accordance with standard techniques from the known sequences of DNA in or associated with a gene linked to VHb or from sequences which can be generated from such genes in accordance with standard techniques.

It will be appreciated that the detecting steps described herein may be carried out directly or indirectly. Other means of indirectly determining allelic type include measuring polymorphic markers that are linked to the particular functional polymorphism, as has been demonstrated for the VNTR (variable number tandem repeats).

Molecular biology comprises a wide variety of techniques for the analysis of nucleic acid and protein sequences. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, Molecular Cloning: A Laboratory Manual, 2 Ed., Cold spring Harbor Laboratory Press, Cold Spring Harbor, N.Y., 1989).

Most of these techniques involve carrying out numerous operations (e.g., pipetting, centrifugation, and electrophoresis) on a large number of samples. They are often complex and time consuming, and generally require a high degree of accuracy. Many techniques are limited in their application by a lack of sensitivity, specificity, or reproducibility.

Nucleic acid hybridization analysis generally involves the detection of a very small number of specific target nucleic acids (DNA or RNA) with an excess of probe DNA, among a relatively large amount of complex non-target nucleic acids.

A reduction in the complexity of the nucleic acid in a sample is helpful to the detection of low copy numbers (i.e. 10,000 to 100,000) of nucleic acid targets. DNA complexity reduction is achieved to some degree by amplification of target nucleic acid sequences. (See, M. A. Innis et al., PCR Protocols: A Guide to Methods and Applications, Academic Press, 1990, Spargo et al., 1996, Molecular & Cellular Probes, in regard to SDA amplification). This is because amplification of target nucleic acids results in an enormous number of target nucleic acid sequences relative to non-target sequences thereby improving the subsequent target hybridization step.

The hybridization step involves placing the prepared DNA sample in contact with a specific reporter probe at set optimal conditions for hybridization to occur between the target DNA sequence and probe. Hybridization may be performed in any one of a number of formats. For example, multiple sample nucleic acid hybridization analysis has been conducted in a variety of filter and solid support formats (See Beltz et al., Methods in Enzymology, Vol. 100, Part et al., Eds., Academic Press, New York, Chapter 19, pp. 266-308, 1985). One format, the so-called "dot blot" hybridization, involves the non-covalent attachment of target DNAs to a filter followed by the subsequent hybridization to a radioisotope labeled probe(s). "Dot blot" hybridization gained wide-spread use over the past two decades during which time many versions were developed (see Anderson and Young, in Nucleic Acid Hybridization—A Practical Approach, Hames and Higgins, Eds., IRL Press, Washington, D.C. Chapter 4, pp. 73-111, 1985). For example, the dot blot method has been developed for multiple analyses of genomic mutations (EPA 0228075 to Nanibhushan et al.) and for the detection of overlapping clones and the construction of genomic maps (U.S. Pat. No. 5,219,726 to Evans).

Additional techniques for carrying out multiple sample nucleic acid hybridization analysis include micro-formatted multiplex or matrix devices (e.g., DNA chips) (see M. Barinaga, 253 Science, pp. 1489, 1991; W. Bains, 10 Bio/Technology, pp. 757-758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757-758, 1992). SBH makes use of all possible n-nucleotide oligomers (n-mers) to identify n-mers in an unknown DNA sample, which are subsequently aligned by algorithm analysis to produce the DNA sequence (See, Drmanac U.S. Pat. No. 5,202,231).

There are two formats for carrying out SBH. The first format involves creating an array of all possible n-mers on a support, which is then hybridized with the target sequence. The second format involves attaching the target sequence to a support, which is sequentially probed with all possible n-mers. Southern, (United Kingdom Patent Application GB 8810400, 1988; E. M. Southern et al., 13 Genomics 1008, 1992), proposed using the first format to analyze or sequence DNA. Southern identified a known single point mutation using PCR amplified genomic DNA. Southern also described a method for synthesizing an array of oligonucleotides on a solid support for SBH. Drmanac et al., (260 Science 1649-1652, 1993), used a second format to sequence several short (116 bp) DNA sequences. Target DNAs were attached to membrane supports ("dot blot" format). Each filter was sequentially hybridized with 272 labeled 10-mer and 1-mer oligonucleotides. Wide ranges of stringency conditions were used to achieve specific hybridization for each n-mer probe. Washing times varied from 5 minutes to overnight using temperatures from 0° C. to 16° C. Most probes required 3 hours of washing at 16° C. The filters had to be exposed from 2 to 18 hours in order to detect hybridization signals.

Generally, a variety of methods are available for detection and analysis of the hybridization events. Depending on the reporter group (fluorophore, enzyme, radioisotope, etc.) used to label the DNA probe, detection and analysis are carried out fluorimetrically, calorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. Thus, detection of hybridization events is dependent upon how specific and sensitive hybridization can be made. Concerning genetic analysis, several methods have been developed that have attempted to increase specificity and sensitivity.

One form of genetic analysis is analysis centered on elucidation of single nucleic acid polymorphisms or ("SNPs"). Factors favoring the usage of SNPs are their high abundance in the human genome (especially compared to short tandem repeats, (STRs)), their frequent location within coding or regulatory regions of genes (which can affect protein structure or expression levels), and their stability when passed from one generation to the next (Landegren et al., Genome Research, Vol. 8, pp. 769-776, 1998).

A SNP is defined as any position in the genome that exists in two variants and the most common variant occurs less than 99% of the time. In order to use SNPs as widespread genetic markers, it is crucial to be able to genotype them easily, quickly, accurately, and cost-effectively. Numerous techniques are currently available for typing SNPs (for review, see Landegren et al., Genome Research, Vol. 8, pp. 769-776, (1998), all of which require target amplification. They include direct sequencing (Carothers et al., BioTechniques, Vol. 7, pp. 494-499, 1989), single-strand conformation polymorphism (Orita et al., Proc. Natl. Acad. Sci. USA, Vol. 86, pp. 2766-2770, 1989), allele-specific amplification (Newton et al., Nucleic Acids Research, Vol. 17, pp. 2503-2516, (1989), restriction digestion (Day and Humphries, Analytical Biochemistry, Vol. 222, pp. 389-395, 1994), and hybridization assays. In their most basic form, hybridization assays function by discriminating short oligonucleotide reporters against matched and mismatched targets. Many adaptations to the basic protocol have been developed. These include ligation chain reaction (Wu and Wallace, Gene, Vol. 76, pp. 245-254, 1989) and minisequencing (Syvanen et al., Genomics, Vol. 8, pp. 684-692, 1990). Other enhancements include the use of the 5'-nuclease activity of Taq DNA polymerase (Holland et al., Proc. Natl. Acad. Sci. USA, Vol. 88, pp. 7276-7280, 1991), molecular beacons (Tyagi and Kramer, Nature Biotechnology, Vol. 14, pp. 303-308, 1996), heat denaturation curves (Howell et al., Nature Biotechnology, Vol. 17, pp. 87-88, 1999) and DNA "chips" (Wang et al., Science, Vol. 280, pp. 1077-1082, 1998).

An additional phenomenon that can be used to distinguish SNPs is the nucleic acid interaction energies or base-stacking energies derived from the hybridization of multiple target specific probes to a single target. (See, R. Ornstein et al., "An Optimized Potential Function for the Calculation of Nucleic Acid Interaction Energies", Biopolymers, Vol. 17, 2341-2360 (1978); J. Norberg and L. Nilsson, Biophysical Journal, Vol. 74, pp. 394-402, (1998); and J. Pieters et al., Nucleic Acids Research, Vol. 17, no. 12, pp. 4551-4565 (1989)). This base-stacking phenomenon is used in a unique format in the current invention to provide highly sensitive Tm differentials allowing the direct detection of SNPs in a nucleic acid sample.

Additional methods have been used to distinguish nucleic acid sequences in related organisms or to sequence DNA. For example, U.S. Pat. No. 5,030,557 by Hogan et al. disclosed that the secondary and tertiary structure of a single stranded target nucleic acid may be affected by binding "helper" oligonucleotides in addition to "probe" oligonucleotides causing a higher Tm to be exhibited between the probe and target nucleic acid. That application, however, was limited in its approach to using hybridization energies only for altering the secondary and tertiary structure of self-annealing RNA strands, which if left unaltered would tend to prevent the probe from hybridizing to the target.

With regard to DNA sequencing, K. Khrapko et al., Federation of European Biochemical Societies Letters, Vol. 256, no. 1,2, pp. 118-122 (1989), for example, disclosed that continuous stacking hybridization resulted in duplex stabilization. Additionally, J. Kieleczawa et al., Science, Vol. 258, pp. 1787-1791 (1992), disclosed the use of contiguous strings of hexamers to prime DNA synthesis wherein the contiguous strings appeared to stabilize priming Likewise, L. Kotler et al., Proc. Natl. Acad. Sci. USA, Vol. 90, pp. 4241-4245, (1993) disclosed sequence specificity in the priming of DNA sequencing reactions by use of hexamer and pentamer oligonucleotide modules. Further, S. Parinov et al., Nucleic Acids Research, Vol. 24, no. 15, pp. 2998-3004, (1996), disclosed the use of base-stacking oligomers for DNA sequencing in association with passive DNA sequencing microchips. Moreover, G. Yershov et al., Proc. Natl. Acad. Sci. USA, Vol. 93, pp. 4913-4918 (1996), disclosed the application of base-stacking energies in SBH on a passive microchip. In Yershov's example, 10-mer DNA probes were anchored to the surface of the microchip and hybridized to target sequences in conjunction with additional short probes, the combination of which appeared to stabilize binding of the probes. In that format, short segments of nucleic acid sequence could be elucidated for DNA sequencing. Yershov further noted that in their system the destabilizing effect of mismatches was increased using shorter probes (e.g., 5-mers). Use of such short probes in DNA sequencing provided the ability to discern the presence of mismatches along the sequence being probed rather than just a single mismatch at one specified location of the probe/target hybridization complex. Use of longer probes (e.g., 8-mer, 10-mer, and 13-mer oligos) was less functional for such purposes.

An additional example of methodologies that have used base-stacking in the analysis of nucleic acids includes U.S. Pat. No. 5,770,365 by Lane et al., wherein is disclosed a method of capturing nucleic acid targets using a unimolecular capture probe having a single stranded loop and a double stranded region which acts in conjunction with a binding target to stabilize duplex formation by stacking energies.

The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced.

Novel spinosyns can also be produced by mutagenesis of the cloned genes, and substitution of the mutated genes for their unmutated counterparts in a spinosyn-producing organism. Mutagenesis may involve, for example: 1) deletion or inactivation of a ketoreductase, dehydratase or enoyl reductase (KR, DH, or ER) domain so that one or more of these functions is blocked and the strain produces a spinosyn having a lactone nucleus with a double bond, a hydroxyl group, or a keto group that is not present in the nucleus of spinosyn A (see Donadio et al., 1993); 2) replacement of an AT domain so that a different carboxylic acid is incorporated in the lactone nucleus (see Ruan et al., 1997); 3) addition of a KR, DH, or ER domain to an existing PKS module so that the strain produces a spinosyn having a lactone nucleus with a saturated bond, hydroxyl group, or double bond that is not present in the nucleus of spinosyn A; or 4) addition or subtraction of a complete PKS module so that the cyclic lactone nucleus has a greater or lesser number of carbon atoms. A hybrid PKS can be created by replacing the spinosyn PKS loading domain with heterologous PKS loading. See, e.g., U.S. Pat. No. 7,626,010. It has further been noted that spinosyns via modification of the sugars that are attached to the spinosyn lactone backbone can include modifications of the rhamnose and/or forosamine moiety or attachment of different deoxy sugars. The Salas group in Spain demonstrated that novel polyketide compounds can be produced by substituting the existing sugar molecule with different sugar molecules. Rodriguez et al. J. Mol. Microbiol Biotechnol. 2000 July; 2 (3):271-6. The examples that follow throughout the application help to illustrate the use of mutagenesis to produce a spinosyn with modified functionality.

The DNA from the spinosyn gene cluster region can be used as a hybridization probe to identify homologous sequences. Thus, the DNA cloned here could be used to locate additional plasmids from the *Saccharopolyspora spinosa* gene libraries which overlap the region described here but also contain previously uncloned DNA from adjacent regions in the genome of *Saccharopolyspora spinosa*. In addition, DNA from the region cloned here may be used to identify non-identical but similar sequences in other organisms. Hybridization probes are normally at least about 20 bases long and are labeled to permit detection.

Various types of mutagenesis can be used in the invention for a variety of purposes. They include, but are not limited to, site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, crystal structure or the like.

The texts and examples found herein describe these procedures. Additional information is found in the following publications and references cited within: Ling et al., Approaches to DNA mutagenesis: an overview, Anal Biochem. 254 (2): 157-178 (1997); Dale et al., Oligonucleotide-directed random mutagenesis using the phosphorothioate method, Methods Mol. Biol. 57:369-374 (1996); Smith, In vitro mutagenesis, Ann. Rev. Genet. 19:423-462 (1985); Botstein & Shortle, Strategies and applications of in vitro mutagenesis, Science 229:1193-1201 (1985); Carter, Site-directed mutagenesis, Biochem. J. 237:1-7 (1986); Kunkel, The efficiency of oligonucleotide directed mutagenesis, in Nucleic Acids & Molecular Biology (Eckstein, F. and Lilley, D. M. J. eds., Springer Verlag, Berlin) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Bass et al., Mutant Trp repressors with new DNA-binding specificities, Science 242:240-245 (1988); Methods in Enzymol. 100: 468-500 (1983); Methods in Enzymol. 154: 329-350 (1987); Zoller & Smith, Oligonucleotide-directed mutagenesis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Improved enzymatic in vitro reactions in the gapped duplex DNA approach to oligonucleotide-directed construction of mutations, Nucl. Acids Res. 16: 7207 (1988); Fritz et al., Oligonucleotide-directed construction of mutations: a gapped duplex DNA procedure without enzymatic reactions in vitro, Nucl. Acids Res. 16: 6987-6999 (1988); Kramer et al., Point Mismatch Repair, Cell 38:879-887 (1984); Carter et al., Improved oligonucleotide site-directed mutagenesis using M13 vectors, Nucl. Acids Res. 13: 4431-4443 (1985); Carter, Improved oligonucleotide-directed mutagenesis using M13 vectors, Methods in Enzymol. 154: 382-403 (1987); Eghtedarzadeh & Henikoff, Use of oligonucleotides to generate large deletions, Nucl. Acids Res. 14: 5115 (1986); Wells et al., Importance of hydrogen-bond formation in stabilizing the transition state of subtilisin, Phil. Trans. R. Soc. Lond. A 317: 415-423 (1986); Nambiar et al., Total synthesis and cloning of a gene coding for the ribonuclease S protein, Science 223: 1299-1301 (1984); Sakamar and Khorana, Total synthesis and expression of a gene for the a-subunit of bovine rod outer segment guanine nucleotide-binding protein (transducin), Nucl. Acids Res. 14: 6361-6372 (1988); Wells et al., Cassette mutagenesis: an efficient method for generation of multiple mutations at defined sites, Gene 34:315-323 (1985); Grundstrom et al., Oligonucleotide-directed mutagenesis by microscale 'shot-gun' gene synthesis, Nucl. Acids Res. 13: 3305-3316 (1985); Mandecki, Oligonucleotide-directed double-strand break repair in plasmids of *Escherichia coli*: a method for site-specific mutagenesis, Proc. Natl. Acad. Sci. USA, 83:7177-7181 (1986); Arnold, Protein engineering for unusual environments, Current Opinion in Biotechnology 4:450-455 (1993); Sieber, et al., Nature Biotechnology, 19:456-460 (2001). W. P. C. Stemmer, Nature 370, 389-91 (1994); and, I. A. Lorimer, I. Pastan, Nucleic Acids Res. 23, 3067-8 (1995). Additional details on many of the above methods can be found in Methods in Enzymology Volume 154, which also describes useful controls for trouble-shooting problems with various mutagenesis methods.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm, which has been incorporated into the GAP program in the GCG software package (available on the internet at the accelrys website, more specifically at <http://www.accelrys.com>), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available on the internet at the accelrys website, more specifically at <http://www.accelrys.com>), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available on the internet at the vega website, more specifically ALIGN-IGH Montpellier, or more specifically at <http://vega.igh.cnrs.fr/bin/align-guess.cgi>) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. (Available on the internet at the ncbi website, more specifically at <www.ncbi.nlm.nih.gov>).

Suitable expression vectors for use in the present invention include prokaryotic and eukaryotic vectors (e.g., plasmid, phagemid, or bacteriophage), include mammalian vectors and plant vectors. Suitable prokaryotic vectors include plasmids such as, but not limited to, those commonly used for DNA manipulation in *Actinomyces*, (for example pSET152, pOJ260, pIJ101, pJV1, pSG5, pHJL302, pSAM2, pKC1250). Such plasmids are disclosed by Kieser et al. ("Practical *Streptomyces* Genetics", 2000). Other suitable vectors can include plasmids such as those capable of replication in *E. coli* (for example, pBR322, ColE1, pSC101, PACYC 184, itVX, pRSET, pBAD (Invitrogen, Carlsbad, Calif.) and the like). Such plasmids are disclosed by Sambrook (cf. "Molecular Cloning: A Laboratory Manual," second edition, edited by Sambrook, Fritsch, & Maniatis, Cold Spring Harbor Laboratory, (1989)) and many such vectors are commercially available. *Bacillus* plasmids include pC194, pC221, pT127, and the like, and are disclosed by Gryczan (In: The Molecular Biology of the Bacilli, Academic Press, NY (1982), pp. 307-329). Suitable *Streptomyces* plasmids include pli101 (Kendall et al., J. Bacteriol. 169:4177-4183, 1987), and *Streptomyces* bacteriophages include but not limited to such as ψC31 (Chater et al., In: Sixth International Symposium on Actinomycetales Biology, Akademiai Kaido, Budapest, Hungary (1986), pp. 45-54). Pseudomonas plasmids are reviewed by John et al. (Rev. Infect. Dis. 8:693-704, 1986), and Izaki (Jpn. J. Bacteriol. 33:729-742, 1978).

Suppression of the expression of particular genes is an important tool both for research and for the development of genetically engineered organisms more fitted for a particular purpose. Gene silencing can be accomplished by the introduction of a transgene corresponding to the gene of interest in the antisense orientation relative to its promoter (see, e.g., Sheehy et al., Proc. Nat'l Acad. Sci. USA 85:8805 8808 (1988); Smith et al., Nature 334:724 726 (1988)), or in the sense orientation relative to its promoter (Napoli et al., Plant Cell 2:279 289 (1990); van der Krol et al., Plant Cell 2:291 299 (1990); U.S. Pat. No. 5,034,323; U.S. Pat. No. 5,231,020; and U.S. Pat. No. 5,283,184), both of which lead to reduced expression of the transgene as well as the endogenous gene.

Posttranscriptional gene silencing has been reported to be accompanied by the accumulation of small (20 to 25 nucleotide) fragments of antisense RNA, which can be synthesized from an RNA template and represent the specificity and mobility determinants of the process (Hamilton & Baulcombe, Science 286:950 952 (1999)). It has become clear that in a range of organisms the introduction of dsRNA (double-stranded RNA) is an important component leading to gene silencing (Fire et al., Nature 391:806 811 (1998); Timmons & Fire, Nature 395:854 (1998); WO99/32619; Kennerdell & Carthew, Cell 95:1017 1026 (1998); Ngo et al., Proc. Nat'l Acad. Sci. USA 95:14687 14692 (1998); Waterhouse et al., Proc. Nat'l Acad. Sci. USA 95:13959 13964 (1998); WO99/53050; Cogoni & Macino, Nature 399:166 169 (1999);

Lohmann et al., Dev. Biol. 214:211 214 (1999); Sanchez-Alvarado & Newmark, Proc. Nat'l Acad. Sci. USA 96:5049 5054 (1999)). In bacteria the suppressed gene does not need to be an endogenous bacterial gene, since both reporter transgenes and virus genes are subject to posttranscriptional gene silencing by introduced transgenes (English et al., Plant Cell 8:179 188 (1996); Waterhouse et al, supra). However, in all of the above cases, some sequence similarity may be preferred between the introduced transgene and the gene that is suppressed.

The examples which follow are set forth to illustrate the present invention, and are not to be construed as limiting thereof.

Examples

Construction of a Hemoglobin Gene Expression Cassette

Figure 1:
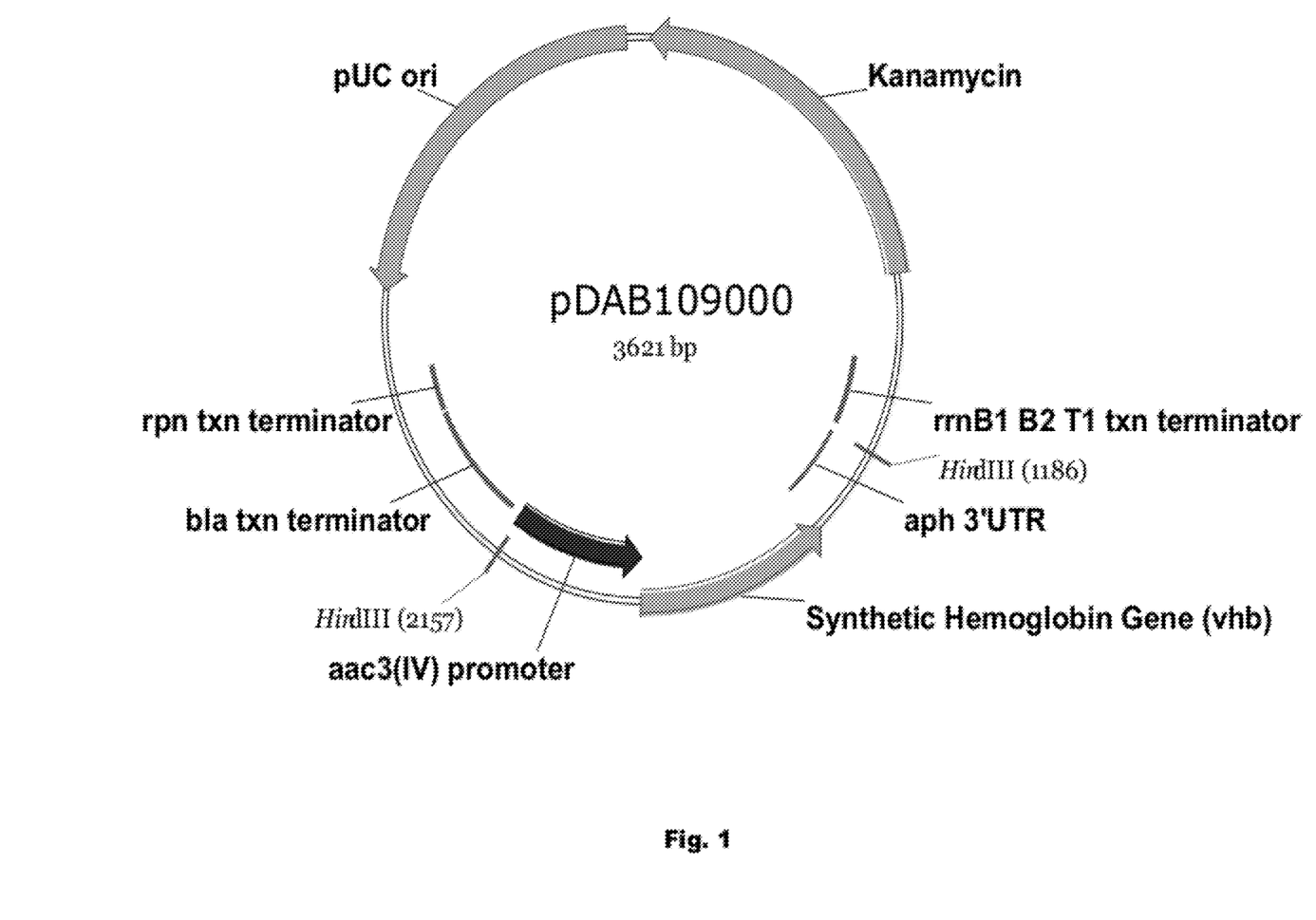
FIG. 1 depicts plasmid pDAB109000 containing the 977 bp synthetic DNA fragment with pJ201.

A hemoglobin gene expression cassette was designed to contain the following key features: i) the apramycin resistance gene (originally from *Klebsiella pneumoniae* under GenBank Accession Number X99313; Kieser et al., 2001) promoter (aac3(IV) promoter) which is functional in *S. spinosa*; ii) codon optimized *Vitreoscilla* hemoglobin gene VHb (Table 1) designed using a *S. spinosa* codon preference table and GeneDesigner software (DNA 2.0, Menlo Park, Calif.); and iii) the aph transcription terminator sequence (Pulido and Jiménez, 1987). The selection and arrangement of these gene elements ensure stable VHb transcription and optimum protein expression, thereby providing robust expression of the hemoglobin protein. The hemoglobin gene expression cassette (SEQ ID NO:1) was synthesized by DNA 2.0 (Menlo Park, Calif.). The resulting 977 bp synthetic HinDIII flanked fragment was cloned into the pJ201 vector (FIG. 1) and was sequenced by DNA2.0 to confirm sequence accuracy prior to shipment. The resulting plasmid was designated as pDAB109000.

facilitate stable integration of the hemoglobin gene expression cassette within the obscurin gene cluster of the genome of *S. spinosa*.

The hemoglobin gene expression cassette was first cloned into vector pIJ773 (John Innes Centre, Norwich, UK) via a conventional cloning method. This cassette, in addition to the apramycin resistance gene and oriT flanked by FRT recombination sequences was then cloned into cosmid 1E3 via PCR targeting (Gust et al., 2002). Briefly, the hemoglobin gene expression cassette was first amplified using pDAB109000 as a template and the following primers, aac3-VHb Forward (SEQ ID NO:2 5'-CGCTGAAAAGCTTCTGACGCCG-3') and aac3-VHb Reverse (SEQ ID NO:3 5'-CAACCCGTAC-CACGGCCTCT-3'). The amplified PCR fragment was digested with HindIII/KpnI to generate two fragments; a 864 bp HindIII/KpnI fragment and a 83 bp HindIII/KpnI fragment. The 864 bp HindIII/KpnI fragment, carrying the hemoglobin gene expression cassette including the transcription terminator, was gel purified and cloned into vector pIJ773 which had been digested with HindIII/KpnI. A total of 38 transformants grown on Luria-Bertani media (LB) containing 50 µg/mL of apramycin were selected for further analysis and confirmation. After overnight growth in liquid LB containing apramycin at 50 µg/mL, cells were harvested by centrifugation at 13,000 RPM in a microcentrifuge for 2 minutes.

Figure 2:
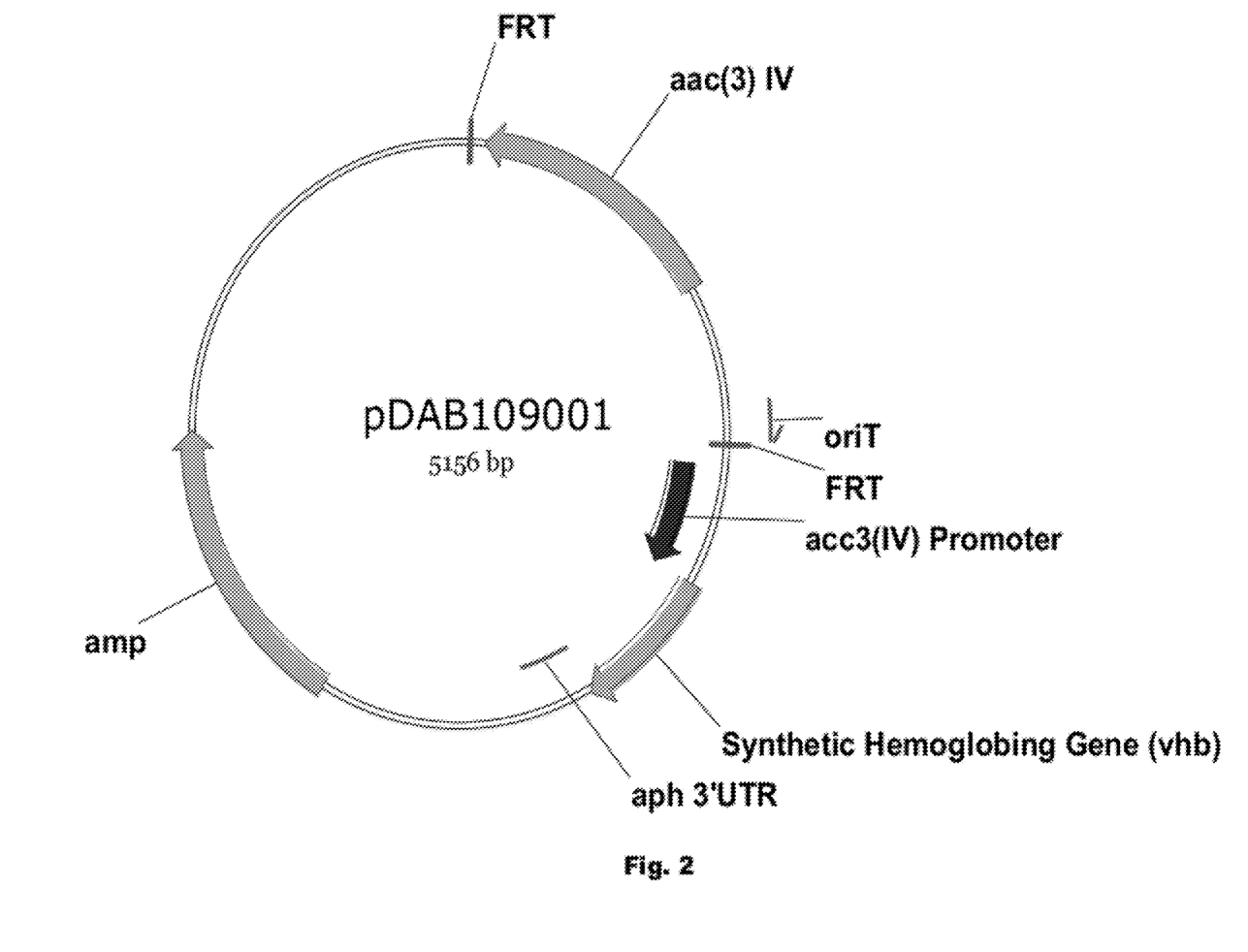
FIG. 2 depicts plasmid pDAB109001, which resulted from cloning of the hemoglobin gene expression cassette into pIJ773.

Cell pellets carrying the control plasmid pDAB109000 produced a reddish color indicating the presence of the hemoglobin protein. However, only seven of the recombinant clones produced visible reddish cell pellets ranging from light red to a more intense red color. These seven clones were selected and advanced to the next step which included plasmid DNA isolation and restriction enzyme digestions. Two of the seven clones, clone 22 and clone 30, produced the desired restriction patterns based on restriction analysis using the following enzymes NdeI, HindIII/KpnI and NdeI/KpnI. The hemoglobin gene region of both clones and the PCR fragment carrying the hemoglobin gene expression cassette were sequenced. The hemoglobin gene region of clone 22 and the PCR fragment was completely sequenced and the sequence data confirmed that the desired synthetic hemoglobin gene was amplified without any errors and was cloned into pIJ773 (FIG. 2). The resulting plasmid was labeled as pDAB109001.

Integration of the FRT::aac3(IV) gene expression cassette::oriT::FRT::synthetic hemoglobin gene expression cassette into cosmid clone 1E3 was carried out as described via a

TABLE 1

Comparison of *Vitreoscilla* hemoglobin gene (VHb) codons and the synthetic hemoglobin gene preferred codons for optimal expression in *S. spinosa*. The synthetic VHb codons are preferred in *S. spinosa* and were selected to replace the preferred codons from the *Vitreoscilla* hemoglobin gene using the GeneDesigner software.

| | Amino Acid | | | | | | | | |
|---|---|---|---|---|---|---|---|---|---|
| | Leu | Arg | Thr | Ile | Lys | Ala | Val | Pro | His |
| *Vitreoscilla* VHb codon | TTA TTG | CGT CGC | ACC ACT | ATT | AAA | GCC GCT GCA | GTT GTA GTC | CCT CCA | CAT |
| Synthetic VHb codon | CTG | CGG | ACG | ATC | AAG | GCG | GTG | CCG | CAC |

| | Amino Acid | | | | | | | |
|---|---|---|---|---|---|---|---|---|
| | Asp | Gly | Ser | Asn | Cys | Phe | Gln | Glu | Tyr |
| *Vitreoscilla* VHb codon | GAT | GGT | TCT | AAT | TGT | TTT | CAA | GAA | TAT |
| Synthetic VHb codon | GAC | GGC | TCG | AAC | TGC | TTC | CAG | GAG | TAC |

Introduction of the Hemoglobin Gene Expression Cassette into Cosmid Clone 1E3

The obscurin gene cluster was chosen as the site for integration of the hemoglobin gene expression cassette because disruption of the obscurin gene cluster does not reduce spinosyn production. The hemoglobin gene expression cassette was cloned into cosmid 1E3 (which contains a genomic DNA partial obscurin gene cluster). This cosmid was engineered to modified PCR Targeting protocol (Gust et al., 2002). The following modifications were incorporated into the protocol: i) the host *E. coli* for introducing the recombinant cosmid clone carrying the hemoglobin gene expression cassette was *E. coli* BW25141/pKD78 acquired from The Coli Genetic Stock Center (CGSC) at Yale University; ii) lambda red recombinase expression plasmid pKD78, derived from pKD46 (Datsenko and Wanner, 2000); and iii) the following PCR primers, obsA Internal Strep stem loop (SEQ ID NO:4 5'-GAAGAAGGCGGCGTCGAACTGGTCGAC-CTCGGTGAGGAAGGTACCTCCGACCGCACGGC-3') and obsA 5' FRT aac3 (SEQ ID NO:5 5'-GGCAATGCGCA-GAGTTCGTAGTGCGGGAGCCATTTGAT-GTGTAGGCTGGAGCTGCTTC-3') were designed and used. The resulting amplification produced a 2,216 bp fragment consisting of (FRT::aac3(IV)::oriT::FRT::VHb) within cosmid clone 1E3.

Integration within cosmid clone 1E3 was designed to occur at the 5' end of obsA, resulting in the removal of 600 bp of the obsA coding sequence. This ensures complete disruption of the first polyketide synthase enzyme within the obscurin gene cluster. Once integrated, the hemoglobin gene expression cassette was orientated in such a way that its coding sequence was in the opposite orientation of the obsA coding sequence. This directionality prevents transcription readthrough from the putative obsA promoter, which could potentially result in undesired transcription. Putative recombinant clones carrying the (FRT::aac3(IV)::oriT::FRT::VHb) fragment were isolated and confirmed by restriction analysis. Restriction digestion using BamHI indicated that the recombinant cosmid clones carrying the hemoglobin gene cassette had different restriction patterns as compared to the parent cosmid clone, 1E3. Moreover restriction digestion using NdeI and ClaI, intended to re-generate the synthetic hemoglobin gene coding sequence, revealed that only the three recombinant clones produced a the 444 bp fragment carrying the entire coding region of the synthetic hemoglobin gene.

Conjugation of the (FRT::aac3(IV)::oriT::FRT::VHb) Gene Expression Cassette into *S. spinosa* Strains Mycelial conjugation between the donor strain, *Escherichia coli* S17, containing the FRT::aac3(IV) gene expression cassette::oriT::FRT::synthetic hemoglobin gene expression cassette within cosmid 1E3 and the spinosyn producing strain, DAS-2, was completed. Mycelial conjugation between the donor strain and the recipient *S. spinosa* strain was carried out according to the method described by Matsushima et al. (1994). Colonies initially identified as resistant to apramycin and nalidixic acid on the conjugation media were patched onto Brain Heart Infusion agar media (BHI) containing 50 μg/mL of apramycin and 25 μg/mL of nalidixic acid to confirm the antibiotic resistance phenotype of the colonies. Colonies having the desired antibiotic resistance phenotype were presumed to contain the FRT::aac3(IV)::oriT::FRT::VHb cassette integrated within the obsA locus of the obscurin gene cluster. To confirm the presence of the apramycin resistance gene, aac3(IV), genomic DNA of the putative transconjugants was isolated using the PURELUTE™ Bacterial Genomic Kit (Edge BioSystems, Gaithersburg, Md.) according to manufacturer's instructions. This genomic DNA (gDNA) was used as template for PCR amplification size confirmation of a 785 bp aac3(IV) DNA fragment using the FAILSAFE™ PCR System (Epicentre Biotechnologies, Madison, Wis.).

Confirmation of the Presence of a Hemoglobin Gene in Transconjugants

To confirm that the synthetic hemoglobin gene was present in the transconjugants, the genomic DNA of a select number of transconjugants was isolated (via the PURELUTE™ Bacterial Genomic Kit) and used as template for PCR amplification of the hemoglobin gene (via the FAILSAFE™ PCR System). Recombinant strains produced a PCR product of 395 bp, corresponding to the size of the hemoglobin gene coding region intended for amplification. The PCR fragments were purified and DNA sequencing of both strands was completed to further confirm the presence of the VHb gene. Alignment of the sequence derived from the PCR fragments with the synthetic hemoglobin gene sequence synthesized by DNA2.0 indicated that these recombinant strains carried the hemoglobin gene with sequence identical to the designed DNA sequence.

Hemoglobin Gene Expression Under Fermentation Conditions

Expression of the synthetic hemoglobin gene in the recombinant strain carrying the hemoglobin gene expression cassette under fermentation conditions was determined Recombinant strains containing the VHb expression cassette were grown under shake flask fermentation conditions, and the corresponding total RNA samples were isolated via the RIBOPURE™-Bacteria kit (Ambion, Austin, Tex.) and prepared for use as template in the RT-PCR assay. Fermentation of the double crossover mutant was performed under conditions described by Burns et al., (WO 2003070908). Analysis of the fermentation broth for the presence of spinosyn factors can be carried out under conditions described by Baltz et al., (U.S. Pat. No. 6,143,526). To confirm the presence of the spinosyn factors in the supernatant, extracts of the fermentation broth were dried down in a SpeedVac overnight followed by partition of the residue between water and ether. The ether layer was dried by evaporation under $N_2$ stream. The sample was then dissolved in acetone-$d_6$ and transferred to an NMR tube for 1D proton NMR acquisition. The NMR profiles were compared to those of spinosyn standards.

Total RNA preparation was treated with DNaseI (Ambion, Austin, Tex.) immediately following RNA purification according to manufacturer's instructions. RT-PCR of the synthetic hemoglobin gene using the isolated total RNA was carried out using OneStep RT-PCR kit (Qiagen, Valencia, Calif.) according to manufacturer's directions. Primers for amplification of the coding region of the synthetic hemoglobin gene were SynHemo Forward (SEQ ID NO:6 5'-CAGAC-GATCAACATCATCAAGGCG-3') and SynHemo Reverse (SEQ ID NO:7 5'-ACCTGGATGAACACGTCCGC-3'). The recombinant strains containing the VHb expression cassette produced a specific fragment of 395 bp corresponding to the hemoglobin gene coding region intended for amplification. In the same assay, total RNA isolated from the non-recombinant control strains did not produce a PCR fragment corresponding in size to the synthetic hemoglobin gene. These results confirmed that a synthetic hemoglobin gene, driven by the apramycin resistance gene promoter, was transcribed and expressed in *S. spinosa* under fermentation conditions.

Effect of Hemoglobin Gene Expression on Spinosad Production

The impact of the hemoglobin gene expression on spinosad (A/D) production was evaluated by growing the recombinant strains under shake flask fermentation conditions as described above. The fermentation results were compared to spinosyn A/D levels produced in the respective parent strain, which does not carry the hemoglobin gene. The number of recombinant strains selected for evaluation in shake flasks was based on the number of transconjugants available for testing and the desire to obtain data, which would determine whether the expression of the synthetic hemoglobin gene produces increased levels of spinosad A/D.

Seven recombinant strains derived from DAS-2 were tested. All of which outperformed the parent strain, DAS-2, in spinosad production. The parent strain accumulated spinosad within the expected range. The statistically significant increase in spinosad A/D production ranged from 4.6% to 12.9% for the strains, which contained the VHb gene (Table 2). The consistency among the recombinant strains in outperforming the control strain in spinosad production under shake flask fermentation conditions resulted in a significant percent increase of spinosad A/D titers. This increase in spinosad titers indicated that the recombinant strains as a whole have acquired enhanced spinosad production capability due to the presence of the synthetic hemoglobin gene in the genome. Expression of the synthetic hemoglobin gene under shake flask fermentation conditions indicates that the expression of the hemoglobin gene increases spinosad production.

TABLE 2

Comparison of DAS-2 and DAS-2 VHb recombinant strain containing a chromosomally integrated VHb gene in spinosad production.

| Strain ID | Major Spinosyn Factors | Spinosyn Titers Relative to Control in Percentage at Day 10 of Fermentation |
|---|---|---|
| DAS-2 | A/D | 100.0 |
| DAS-2 VHb1 | A/D | 107.4 |
| DAS-2 VHb4 | A/D | 104.6 |
| DAS-2 VHb5 | A/D | 108.0 |
| DAS-2 VHb6 | A/D | 110.5 |
| DAS-2 VHb7 | A/D | 112.9 |
| DAS-2 VHb8 | A/D | 110.4 |
| DAS-2 VHb9 | A/D | 105.6 |

Based on the fermentation results reported above, the following recombinant strains, DAS-2 VHb7 and DAS-2 VHb8, were cryogenically preserved in 20% glycerol using actively growing vegetative cultures. A dedicated shake flask fermentation study was carried out to: i) evaluate the cryo preserved strains; ii) ensure reproducibility of the fermentation results; and iii) provide evidence for advancement of select strains for future work. In this study the control strains produced spinosad at the expected levels, and the entire study was conducted without any unexpected deviations from the operating protocol. Each recombinant strain outperformed both control strains during and at the end of the fermentation cycle confirming the initial observations from the shake flask fermentation studies. The increase in spinosad levels relative to the control strains from the recombinant strains was statistically significant.

The obscurin polyketide synthase gene cluster was used for integration and expression of a codon optimized hemoglobin gene in *S. spinosa* strain, DAS-2. Integration and expression of the hemoglobin gene resulted in improved A/D production in the shake flask fermentation of *S. spinosa*, DAS-2.

All patents and publications referenced are incorporated by reference herein in their entirety. The foregoing is illustrative of the present invention, and is not to be construed as limiting thereof. The invention is defined by the following claims, with equivalents of the claims to be included therein.

What is claimed is:

1. A method for increasing a spinosyn titer in an base *Saccharopolyspora spinosa* strain, the method comprising:
integrating a polynucleotide encoding an oxygen binding protein into a base *S. spinosa* strain to produce a modified *S. spinosa* strain; and
   expressing the polynucleotide in the modified *S. spinosa* strain;
   wherein the titer of a spinosyn is increased by at least 4.6% in the modified *S. spinosa* strain relative to the titer of the spinosyn in the base *S. spinosa* strain as may be determined by comparing the spinosyn titer of the base *S. spinosa* strain to the spinosyn titer of the modified *S. spinosa* strain after 10 days of fermentation under conditions appropriate for the production of spinosyn.

2. The method of claim 1 wherein the oxygen binding protein is a globin protein.

3. The method of claim 2 wherein the globin protein is selected from the group consisting of *Vitreoscilla* hemoglobin, *Alcaligenes eutrophus* flavohemoprotein, horse heart myoglobin, *Escherichia coli* hemoprotein, *Bacillus subtilis* hemoprotein, yeast flavohemoglobin, soybean leghemoglobin, lupin leghemoglobin, and sperm whale myoglobin.

4. The method of claim 2 wherein the globin protein is *Vitreoscilla* hemoglobin or a functional polymorph thereof that increases spinosyn titers.

5. The method of claim 1 wherein the oxygen binding protein is integrated into chromosomal DNA in a neutral site in a *S. spinosa* genome.

6. The method of claim 1 wherein the spinosyn titers that are increased are selected from the group consisting of spinosyn A+D, spinosyn J+L, spinosyn A and spinosyn J.

7. A method of producing spinosyn production the method comprising:
   culturing a *Saccharopolyspora spinosa* that expresses a heterologous gene encoding an oxygen-binding protein under conditions appropriate for production of spinosyn; and collecting spinosyn from a culture of a spinosyn producing organism that expresses a heterologous gene encoding the oxygen-binding protein.

8. The method of claim 7 wherein the heterologous gene is integrated into a chromosome of the *S. spinosa.*

9. A method for integrating a polynucleotide encoding an oxygen binding protein into chromosomal DNA of a strain of *Saccharopolyspora spinosa* species comprising the following steps:
   creating a phage library to identify a genomic locus;
   cloning two genomic DNA fragments from the genomic locus, wherein one genomic fragment is cloned upstream of the polynucleotide encoding an oxygen binding protein, and the second genomic fragment is cloned downstream of said polynucleotide;
   introducing the genomic fragments into a strain of *S. spinosa* by transformation;
   obtaining transconjugants; and,
   screening said transconjugants for presence of said polynucleotide.

10. The method of claim 9 wherein the polynucleotide contains a gene expression cassette.

11. The gene expression cassette of claim 10, wherein the gene expression cassette contains an antibiotic selectable marker.

12. The gene expression cassette of claim 10, wherein the gene expression cassette contains a spinosyn enhancing gene expression cassette.

13. The method of claim 9 wherein the oxygen binding protein is a globin protein.

14. The method of claim 13 wherein the globin protein is selected from the group consisting of *Vitreoscilla* hemoglobin, *Alcaligenes eutrophus* flavohemoprotein, horse heart myoglobin, *E. coli* hemoprotein, *B. subtilis* hemoprotein, yeast flavohemoglobin, soybean leghemoglobin, lupin leghemoglobin, and sperm whale myoglobin.

15. The method of claim 9 wherein the chromosomal DNA selected is in a neutral site in a *S. spinosa* genome.

16. The method of claim 9 wherein the chromosomal DNA selected is an obscuring polyketide synthase cluster.

17. An recombinant *S. spinosa* organism, wherein the organism further expresses a heterologous oxygen binding protein.

18. The organism of claim 17, wherein the oxygen-binding protein is a globin protein.

19. The organism of claim 18, wherein the globin protein is selected from the group consisting of *Vitreoscilla* hemoglobin, *Alcaligenes eutrophus* flavohemoprotein, horse heart myoglobin, *E. coli* hemoprotein, *B. subtilis* hemoprotein, yeast flavohemoglobin, soybean leghemoglobin, lupin leghemoglobin, and sperm whale myoglobin.

20. The organism of claim 17, wherein the spinosyn is selected from the group consisting of spinsoyn A+D, spinosyn J+L, spinosyn A and spinosyn J.

21. The organism of claim 18 wherein the globin protein is *Vitreoscilla* hemoglobin or a functional polymorph thereof that increases spinosyn titers.

* * * * *